(12) United States Patent
Ryu et al.

(10) Patent No.: US 7,074,891 B2
(45) Date of Patent: Jul. 11, 2006

(54) LEUKOCYTE STIMULATING PEPTIDES

(75) Inventors: Sung-Ho Ryu, Pohang (KR); Yoe-Sik Bae, Busan (KR); Eun-Young Park, Pohang (KR); Pann-Ghill Suh, Pohang (KR)

(73) Assignees: POSCO, Pohang-Shi (KR); Postech Foundation, Pohang-Shi (KR)

( * ) Notice: Subject to any disclaimer, the term of this patent is extended or adjusted under 35 U.S.C. 154(b) by 160 days.

(21) Appl. No.: 10/774,147

(22) Filed: Feb. 5, 2004

(65) Prior Publication Data

US 2004/0248255 A1 Dec. 9, 2004

(51) Int. Cl.
C07K 7/06 (2006.01)
C07K 7/08 (2006.01)

(52) U.S. Cl. ...................... 530/326; 530/328; 530/329; 530/330

(58) Field of Classification Search ...................... None
See application file for complete search history.

(56) References Cited

U.S. PATENT DOCUMENTS

2002/0072495 A1  6/2002 Chertov et al.

FOREIGN PATENT DOCUMENTS

| WO | WO 00/31261 A2 | 6/2000 |
| WO | WO 01/96373 A2 | 12/2001 |
| WO | WO 02/058714 A2 | 8/2002 |
| WO | WO 03/031461 A2 | 4/2003 |
| WO | WO 03/031603 A1 | 4/2003 |

OTHER PUBLICATIONS

Wu et al., Roles of phospholipid signaling in chemoattractant-induced responses, Journal of Cell Science, 2000; 113:2935-2940.
Schmitt et al., Induction of T cell development and establishmet of T cell competence from embryonic stem cells differentiated in vitro, Nature Immunology, 2004; 5:410-417.
Farooqui et al., Phospholipase A2 and Its Role in Brain Tissue, Journal of Neurochemistry, 1997, 69:889-901.
Gijon and Leslie, Regulation of arachidonic acid release and cystosolic phospholipase A2 activation, Journal of Leukocyte Biology, 1999; 65:330.
Grynkiewicz et al., A New Generation of Ca2+ Indicators with Greatly Improved Fluorescence Properties, Journal of Biological Chemistry, 1985; 260:3440-3450.
Hayashi et al., Synthetic Hexa- and Heptapeptides that inhibit IL-8 from Binding to and Activating Human Blood Neutrophils, The Journal of Immunology, 1995; 154:814-824.
He et al., The Synthetic Peptide Trp-Lys-tyr-Met-Val-D-Met is a potent chemotactic Agonist for Mouse Formyl Peptide Receptor, The Journal of Immunology, 2000; 165:4598-4605.
Hiemstra et al., Definition of Natural T Cell Antigens with Mimcry Epitopes Obtained from Dedicated Synthetic Peptide Libraries, The Journal of Immunology, 1998;161:4078-4082.
Itoh et. al., Expression profile of Active Genes in Granulocytes, Blood, 1998; 4: ;1432-1441.
Liscovitch et al., Phospholipase D: molecular and cell biology of a novel gene family, Biochem. J., 2000; 345-401-415.
M'Rabet et al., Differential fMet-Leu-Phe- and Plateletactivating Factor-induced Signaling Toward Rat Activation—, Journal of Biological Chemistry, 1999; 274:21847-21852.
Murthy and Makhlouf, Differential Regulation of Phospholipid A2(PLA2)-dependent. Ca2+ Signaling in smooth muscle—, Journal of Biological Chemistry, 1998; 273:34519-34526.
Pan et al., fMet-Leu-Phe Stimulates Proinflammatory Cytokine Gene Expression in Human Peripheral Blood Monocytes: The Role of—, Journal of Immunology, 2000, 164:404-411.
Prossnitz et al., Signal Transducing Properties of the N-formyl Peptide Receptor Expressed in Undifferentiated HL60 Cells, Journal of Immunology, 1993; 151:5704-5715.
Puri, Phospholipase A2: Its role in ADP- and thrombin-induced platelet actication mechanisms, International Journal of Biochemistry and Cell Biology, 1998; 30:1107-1122.
Rabin et al., Chemokine Responses on T Cells are achieved through regulation of both receptor expression and signaling, Journal of Immunology, 1999; 162:3840-3850.
Robson et al., Differential Regulation of Chemokine Production in Human Peritoneal Mesothelial Cells: IFN Controls Neutrophil—, Journal of Immunology, 2001; 167:1028-1038.
Aramburu et al., Affinity-Driven peptide selection of an NFAT Inhibitor More Selective than Cyclosporin-A, Science., 1999; 285:2129-2133.
Badolato et al., Serum Amyloid A Induces Calcium Mobilization and Chemotaxis of Human Monocytes by Activating a Pertussic Toxin—,Journal of Immunology, 1995: 155:4004-4010.
Bae et al., Identification of novel chemoattractant peptides for human leukocytes, Blood, 2001; 97:2854-2862.
Bae et al., Trp-Lys-Tyr-Met-Val-D-Met stimulates superoxide generation and killing of *Staphylococcus aureus*—, Journal of Leukocyte Biology, 1999; 65:241-248.

(Continued)

*Primary Examiner*—Robert A. Wax
(74) *Attorney, Agent, or Firm*—Joseph Hyosuk Kim; JHK Law

(57) ABSTRACT

The present application describes peptides that stimulate arachidonic acid release in target cells. The application also discloses peptides that cause intracellular calcium release.

15 Claims, 9 Drawing Sheets

OTHER PUBLICATIONS

Bae et al., Independent Functioning of Cytosolic Phospholipase A2 Phospholipase D1 in Trp-Lys-Tyr-Met-Val-D-Met-Induced—, Journal of Immunology, 2000; 164:4089-4096.

Baek et al., Indentification of the Peptides that stimulate the Phosphoinositide Hydrolysis in Lymphocyte Cell Lines—, Journal of Biological Chemistry, 1996; 271:8170-8175.

Beradi et al., Basic Fibroblast Growth Factor Mediates its Effects on Committed Myeloid Progenitors by Direct Action and Has No Effect—, Blood, 1995; 86:2123-2129.

Boen et al., Identification of T Cell Ligands in a Library of Peptides Covalently Attached to HLA-DR4, Journal of Immunology, 2000; 165:2040-2047.

Brill et al., Augmentation of RANTES-Induced Extracellular Signal-Regulated Kinase Signaling and T Cell Adhesion by —, Journal of Immunology, 2001; 166:7121-7127.

Dana et al., Essential Requirement of Cytosolic Phospholipase A2 for Activation of the Phagocyte NADPH Oxidase, Journal of Biological Chemistry, 1998; 273:441-445.

Dooley et al., Selective Ligands for the *** Opiod Receptors Identified from a Single Mixture Based Tetrapeptide—, Journal of Biological Chemistry, 1998; 273:18848-18856.

Robinson et al., Activation of Phospholipase A2 in human neutrophils by polyunsaturated fatty acids and its role in stimulation of—, Biochem. J., 1998; 336:611-617.

Sano et al., Human Galectin-3 is a Novel Chemoattractant for Monocytes and Macrophages, Journal of Immunology, 2000; 165:2156-2164.

Seo et al., A Peptide with Unique Receptor Specificity, Journal of Immunology, 1997; 158:1895-1901.

Sugden and Clerk, Regulation of the ERK Subgroup of MAP Kinase Cascades Through G Protein-Coupled Receptors, Cell. Signal., 1997; 9:337-351.

Wilson et al., Immunogenicity.I. Use of Peptide Libraries to Identify Epitopes that activate clonotypic CD4+ T Cells and Induce—, Journal of Immunology, 1999; 163:6424-6434.

Woo et al., Leukotriene B4 Stimulates Rac-ERK Cascade to Generate Reactive Oxygen Species that Mediates Chemotaxis, Journal of Biological Chemistry, 2002; 277:8572-8578.

Marshall et al., "Involvement of Cytosolic Phospholipase A2 and Secretory Phospholipase A2 in Arachidonic Acid Release from Human Neutrophils", The Journal of Immunology (2000), 164: 2084-2091.

Lukas et al., "Identification of Novel Classes of Protein Kinase inhibitors Using Combinatorial Peptide Chemistry Based on Functional Genomics Knowledge", J. Med. Chem (1999), 42: 910-919.

Retrieved from EBI accession no. AAM87955.

Harmenberg et al., "Search for Epitopic Sites of Antibodies to Germ Cell Alkaline Phosphatase", Cancer Communications (1991), 3(10/11): 305-311.

LEUKOCYTE STIMULATING PEPTIDES

BACKGROUND OF THE INVENTION

1. Field of the Invention

The invention relates to a target cell stimulating peptide. The invention is also directed to a method of making the target cell stimulating peptide. Further, the invention is directed to a method of using the target cell stimulating peptide as a chemoattractant.

2. General Background and State of the Art:

Neutrophils play a key role in innate immune responses. Diverse extracellular agonists modulate neutrophil function by stimulating the activities of intracellular enzymes (Robson et al. *J. Immunol.* 2001. 167: 1028–1038; M'Rabet et al. *J. Biol. Chem.* 1999. 274: 21847–21852). Recently, many reports have demonstrated the critical involvement of phospholipases in neutrophil immune response (Gijon et al. *J. Leukoc. Biol.* 1999. 65: 330–336; Wu et al. *J. Cell Sci.* 2000. 113: 2935–2940; Liscovitch et al. *Biochem. J.* 2000. 345: 401–415). Among these phospholipases, phospholipase $A_2$ ($PLA_2$) is an important enzyme that mediates several immune responses. $PLA_2$ hydrolyzes the fatty acyl group from the sn-2 position of phospholipid and concomitantly generates lysophospholipid (Gijon et al. *J. Leukoc. Biol.* 1999. 65: 330–336; Puri et al. Int. *J. Biochem. Cell Biol.* 1998. 30: 1107–1122). Arachidonic acid (AA), the product of $PLA_2$ activity, has been implicated in the regulation of various cellular responses, including calcium influx and superoxide generation in phagocytic cells (Murthy et al. *J. Biol. Chem.* 1998. 273: 34519–34526; Robinson et al. *Biochem. J.* 1998. 336: 611–617).

Mammalian cells contain several isozymes of $PLA_2$, namely, cytosolic $PLA_2$ ($cPLA_2$), calcium-independent $PLA_2$, and secretory $PLA_2$ (Gijon et al. *J. Leukoc. Biol.* 1999. 65: 330–336; Farooqui et al. *J. Neurochem.* 1997. 69: 889–901). Among the $PLA_2$ isozymes, $cPLA_2$ is regarded to play an important role in agonist-induced AA release and in the regulation of lysophospholipid levels in cells (Gijon et al. *J. Leukoc. Biol.* 1999. 65: 330–336). Recently Dana et al. developed $cPLA_2$-deficient mice and confirmed the role of $cPLA_2$ in their eicosanoid production (Dana et al. *J. Biol. Chem.* 1998. 273: 441–445). Set against this background, $cPLA_2$ is considered to be an important pharmacological target for several physiological responses. With this role of $PLA_2$ in mind, particularly with respect to neutrophil function, we undertook to identify new ligands that modulate $PLA_2$ activity, and the characterization of their action mechanisms.

Several recent studies have reported the use of combinatorial peptide libraries to identify sequences involved in various biological responses (Boen et al. *J. Immunol.* 2000. 165: 2040–2047; Wilson et al. *J. Immunol.* 1999. 163: 6424–6434; Hiemstra et al. *J. Immunol.* 1998. 161: 4078–4082). An easy and powerful method for identifying peptide sequences in certain biological reactions was developed by Houghten et al. (Dooley et al. *Methods Mol. Biol.* 1998. 87: 13–24). This method, which uses a positional scanning synthetic peptide combinatorial library (PS-SPCL), has been used for various purposes, including the identification of human immunodeficiency virus protease inhibitors, interleukin-8-specific antagonists, the inhibitor for the nuclear factor of activated T cells, and the ligands of opioid receptors, and peptides responsible for modulating leukocytic cell activity (Owens et al. *Biochem. Biophys. Res. Commun.* 1991. 181: 402–408; Hayashi et al. *J. Immunol.* 1995. 154: 814–824; Aramburu et al. *Science.* 1999. 285: 2129–2133; Dooley et al. *J. Biol. Chem.* 1998. 273: 18848–18856; Baek et al. *J. Biol. Chem.* 1996. 271: 8170–8175).

In the present invention, we adopted the PS-SPCL method to identify the peptides that are responsible for AA release in neutrophil-like differentiated HL60 (dHL60) cells. We found 24 peptides that stimulate AA release in dHL60 cells, and found that these peptides act as chemoattractants for human phagocytes. Conversely, on the topic of the receptors of these peptides, we found that several peptides bound to the formyl peptide receptor like 1 (FPRL1). Some of the peptides were also found to bind to other receptor(s) expressed in HL60 cells. In addition, each peptide was found to be capable of stimulating shared and distinct intracellular signaling pathways.

SUMMARY OF THE INVENTION

The invention provides for small polypeptides that induce target cells to migrate, to release arachidonic acid, induce production of superoxide, or activate $PLA_2$.

The invention is further directed to the following.

Aspects of the invention include a polypeptide, which is about 4 to 20 amino acids in length, and which comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, or SEQ ID NO:35. The polypeptide may be 4 to 15, 4 to 10, 4 to 7, or 6 amino acids in length.

Another aspect of the invention includes an antibody that specifically binds to the polypeptide described above. The antibody may be a monoclonal antibody.

A further aspect of the invention includes an isolated nucleic acid encoding the polypeptide described above. The nucleic acid may include an expression vector comprising the nucleic acid encoding the polypeptide described above. Another further aspect of the invention includes a host cell comprising the expression vector.

Other aspects of the invention include a method of making the polypeptide described above, comprising (a) synthesizing a polypeptide, which is 4 to 20 amino acids in length; (b) contacting the polypeptide with a target cell; and (c) determining whether the cells release an arachidonic acid, wherein induction of the arachidonic acid indicates the presence of the polypeptide. The target cell may be a leukocyte or a phagocyte.

An additional aspect of the invention includes a method of inducing expression of arachidonic acid in a target cell, comprising (a) generating a recombinant viral or plasmid vector comprising a DNA sequence encoding the polypeptide described above operably linked to a promoter; and (b) administering the viral or plasmid vector to a patient in need thereof, such that expression of said DNA sequence within the target cell results in expression of the arachidonic acid. The target cell may be a leukocyte or phagocyte.

An additional aspect of the invention includes a method of inducing expression of arachidonic acid in a target cell comprising contacting the target cell with the polypeptide described above. The target cell may be a leukocyte or phagocyte.

An additional aspect of the invention includes a method of activating $PLA_2$ in a target cell comprising contacting the cell with the polypeptide described above. The $PLA_2$ may be c $PLA_2$. The target cell may be a leukocyte or phagocyte.

Another aspect of the invention includes a method of producing superoxide in a target cell comprising contacting the cell with the polypeptide described above. The target cell may be a leukocyte or phagocyte.

An additional aspect of the invention includes a method of causing movement of a target cell, comprising contacting the cell with the polypeptide described above. The target cell preferably expresses FPRL1 but does not express FPR.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings, which are given by way of illustration only, and thus are not limitative of the present invention, and wherein.

DETAILED DESCRIPTION OF THE PREFERRED EMBODIMENTS

Figure 1:
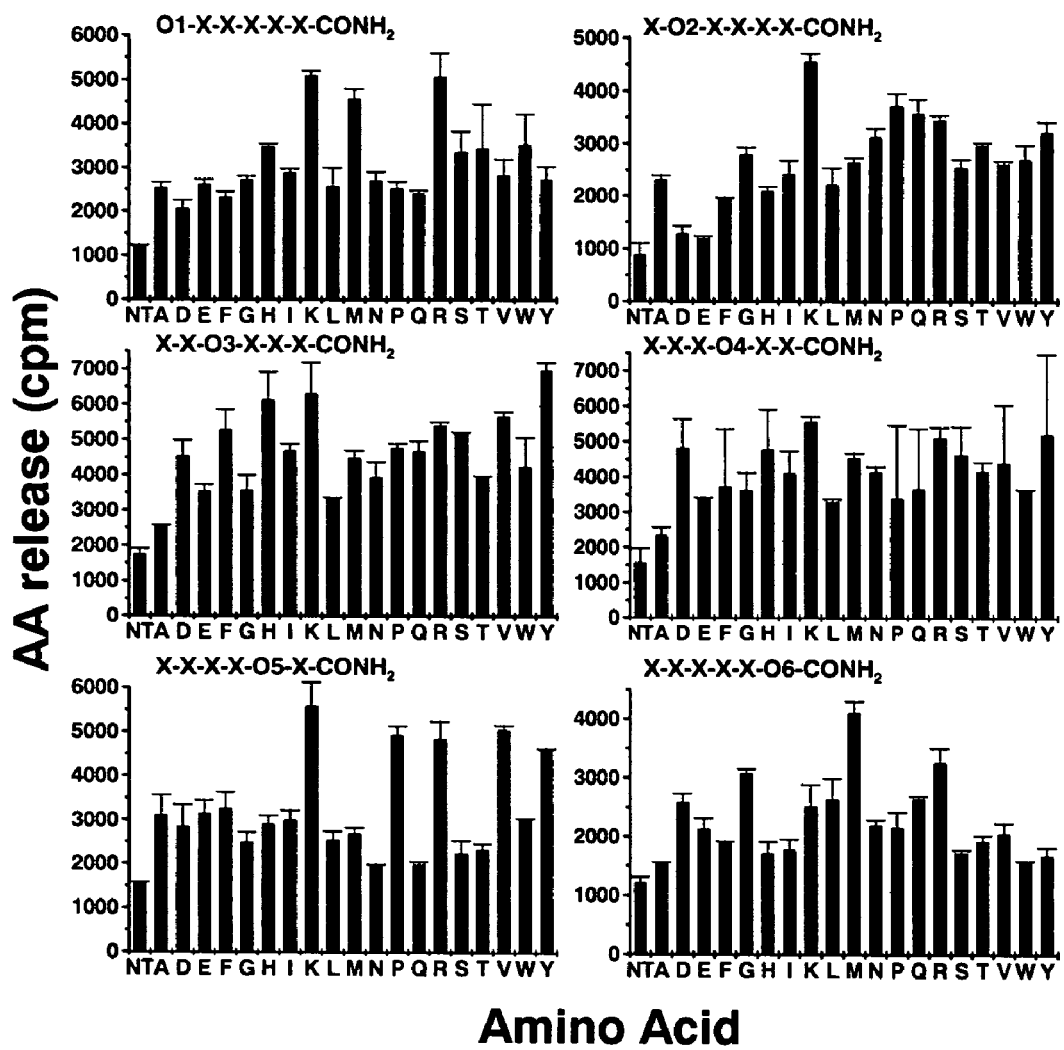
FIG. 1 shows an initial screening of the PS-SPCLs for peptides stimulating AA release in dHL60 cells. Each panel shows the results obtained with peptide pools containing known amino acids at each of the six positions of the hexapeptide. The six positions were individually defined (O1, O2 etc.) by one of the 19 L-amino acids. The remaining five positions consist of mixtures (X) of the 19 L-amino acids (except cysteine). ($^3$H) AA-labeled differentiated HL60 cells ($1 \times 10^6$ cells/100 µl) were used for each assay. AA release was measured as described in the Examples. The results are from representative experiments, which were conducted in quadruplicate.

In the present application, "a" and "an" are used to refer to both single and a plurality of objects.

As used herein, "about" or "substantially" generally provides a leeway from being limited to an exact number. For example, as used in the context of the length of a polypeptide sequence, "about" or "substantially" indicates that the polypeptide is not to be limited to the recited number of amino acids. A few amino acids add to or subtracted from the N-terminus or C-terminus may be included so long as the functional activity such as its binding activity is present.

As used herein, "amino acid" and "amino acids" refer to all naturally occurring L-α-amino acids. This definition is meant to include norleucine, ornithine, and homocysteine.

Either single or three letter abbreviations for the amino acids are used throughout the application, and may be used interchangeably, and have the following meaning: A or Ala=alanine; R or Arg=arginine; N or Asn=asparagine; D or Asp=aspartic acid; C or Cys=cysteine; Q or Gln=glutamine; E or Glu=glutamic acid; G or Gly=glycine; H or His=histidine; I or Ile=isoleucine; L or Leu=leucine; K or Lys=lysine; M or Met=methionine; F or Phe=phenylalanine; P or Pro=proline; S or Ser=serine; T or Thr=threonine; W or Trp=tryptophan; Y or Tyr=tyrosine; and V or Val=valine.

As used herein, in general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, and so on.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

As used herein, "cell stimulating polypeptide" or "cell activating polypeptide" refers to a polypeptide that stimulates cells to produce arachidonic acid, increase $Ca^{++}$ or act as a chemoattractant.

As used herein, "carriers" include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, "chemoattractant" refers to a substance that elicits directional migration of cells in response to the concentration gradient of the molecule.

As used herein, "effective amount" is an amount sufficient to effect beneficial or desired clinical or biochemical results. An effective amount can be administered one or more times. For purposes of this invention, an effective amount of a target cell activator compound is an amount that is sufficient to palliate, ameliorate, stabilize, reverse, slow or delay the progression of a condition. In a preferred embodiment of the invention, the "effective amount" is defined as an amount of compound capable of stimulating target cells, preferably leukocytes, to produce arachidonic acid.

As used herein, "host cell" includes an individual cell or cell culture which can be or has been a recipient of a vector of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo with a vector comprising a polynucleotide encoding an angiogenic factor.

As used herein, "leukocyte" refers to a pale, nucleated cell that acts as a part of the immune system by destroying invading cells and removing debris, and include such cells as granulocyte, lymphocyte, macrophage and monocyte.

Granulocytes or polymorphonuclear leukocytes are marked by the presence of granules in their cytoplasm, and are active in allergic immune reactions such as arthritic inflammation and rashes. Granulocytes include basophils, eosinophils and neutrophils.

Neutrophils move out of blood vessels into infected tissue in order to attack foreign substances such as allergen, bacteria, and so on. Normally, a serious bacterial infection causes the body to produce an increased number of neutrophils, resulting in a higher than normal white blood cell count. Neutrophils perform their function partially through phagocytosis, a process by which they "eat" other cells and foreign substances. For example, the pus in a boil (abscess) is made up mostly of neutrophils Lymphocytes are a type of non-granular leukocyte that mainly stays in lymphatic tissue (e.g., the lymph nodes) and is active in immune responses, including the production of antibodies.

Macrophage is a type of large leukocyte that travels in the blood but can leave the bloodstream and enter tissue; like other leukocytes, it protects the body by digesting debris and foreign cells.

Monocyte is a type of large, round leukocyte that engulfs and breaks down debris and invading cells. Monocytes are formed in bone marrow and have round or kidney-shaped nuclei.

As used herein, "ligand" refers to any molecule or agent, or compound that specifically binds covalently or transiently to a molecule such as a polypeptide. When used in certain context, ligand may include antibody. In other context, "ligand" may refer to a molecule sought to be bound by another molecule with high affinity.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein, "phagocytes" refer to any cell that engulfs and devours another.

As used herein, "purified" or "isolated" molecule refers to biological molecules that are removed from their natural environment and are isolated or separated and are free from other components with which they are naturally associated.

As used herein, "sample" or "biological sample" is referred to in its broadest sense, and includes any biological sample obtained from an individual, body fluid, cell line, tissue culture, or other source which may contain target cells, preferably leukocytes or phagocytes, depending on the type of assay that is to be performed. As indicated, biological samples include body fluids, such as semen, lymph, sera, plasma, urine, synovial fluid, spinal fluid and so on. Methods for obtaining tissue biopsies and body fluids from mammals are well known in the art.

As used herein, "sequence identity", is defined as the percentage of amino acid residues in a candidate sequence that are identical with the amino acid residues in a native polypeptide sequence after aligning the sequences and introducing gaps, if necessary, to achieve the maximum percent sequence identity, and not considering any conservative substitutions as part of the sequence identity. The % sequence identity values are generated by the NCBI BLAST2.0 software as defined by Altschul et al., (1997), "Gapped BLAST and PSI-BLAST: a new generation of protein database search programs", Nucleic Acids Res., 25:3389–3402. The parameters are set to default values, with the exception of the Penalty for mismatch, which is set to −1.

As used herein, the term "specifically binds" refers to a non-random binding reaction between two molecules, for example between the inventive polypeptide and the target cells such as leukocytes or phagocytes.

As used herein, "subject" is a vertebrate, preferably a mammal, more preferably a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

As used herein, "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, complexed with compounds such as polyethylene glycol (PEG) to immunologically "mask" the molecule and/or increase half-life, or conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

Screening for Peptides that Cause Target Cell Stimulation

In the present invention, we screened combinatorial peptide libraries, preferably hexapeptides. We screened a library containing more than 47 million different peptide sequences, and identified 24 hexapeptides that could stimulate AA release in dHL60 cells. In terms of their physiological roles, the peptides were found to enhance superoxide generation and the chemotactic migration of phagocytic cells. Through experiments on the receptor specificity or the signaling specificity of the peptides, we found that the peptides may induce either overlapping or distinct intracellular signals via a common receptor, FPRL1, or via an unidentified receptor in leukocytic cells.

Figure 7:
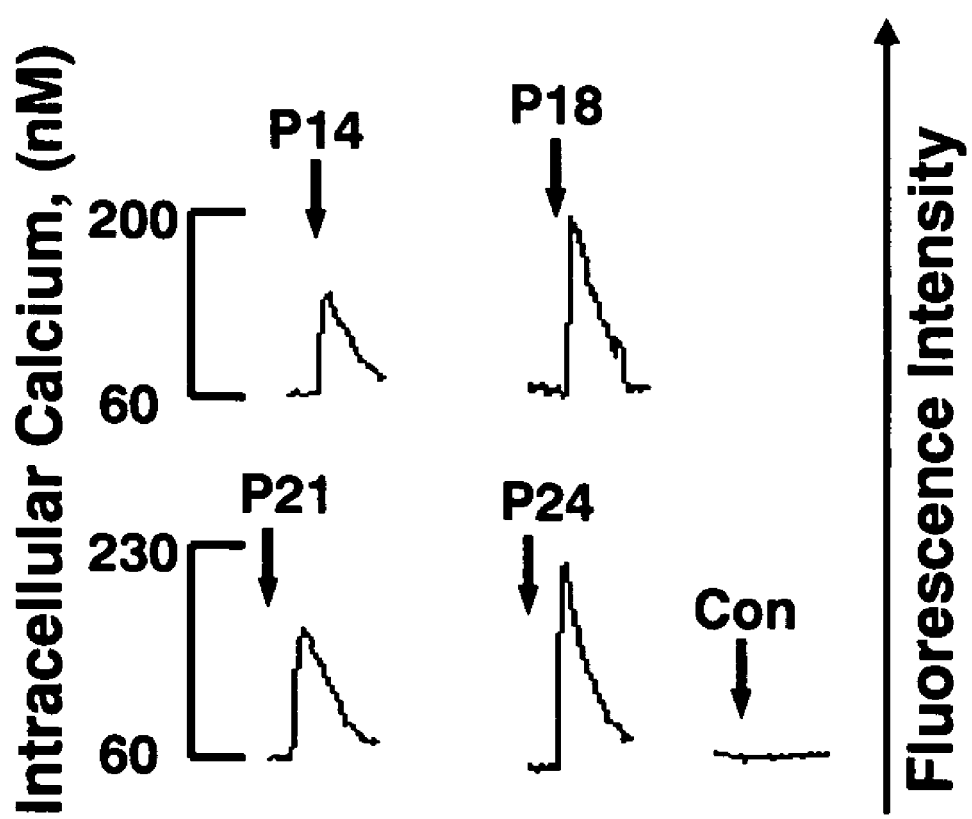
FIG. 7 shows effect of peptides on $[Ca^{2+}]_i$ rise in FPRL1-expressing RBL-2H3 cells. Fura-2 loaded FPRL1-expressing RBL-2H3 cells were stimulated with 10 µM of each peptide and $[Ca^{2+}]_i$ increase was monitored. The traces shown are from a single experiment representative of at least three independent experiments.
Figure 8:
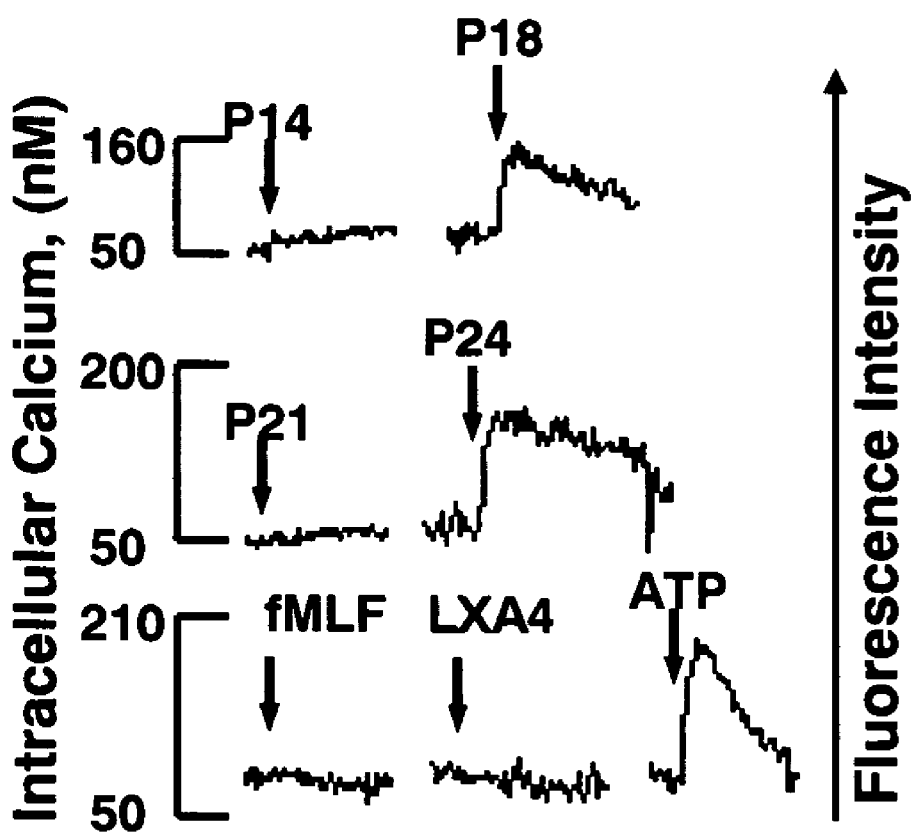
FIG. 8 shows effect of peptides on $[Ca^{2+}]_i$ increase in HL60 cells. Fura-2 loaded HL60 cells were stimulated with 10 µM of each peptide and $[Ca^{2+}]_i$ increase was monitored. The traces shown are from a single experiment representative of at least three independent experiments.

On investigating the receptor specificity of the peptides, we found that 4 peptides could stimulate $[Ca^{2+}]_i$ increase in FPRL1-expressing RBL-2H3 cells but not in FPR-expressing RBL-2H3 cells (FIG. 7). Of the 4 peptides, only two stimulated undifferentiated HL60 cells (FIG. 8). Since undifferentiated HL60 cells do not express FPRL1, the target receptors for these 2 peptides (P18 and P24) could not be FPRL1. From experiments on the effects of PTX on peptide-induced $[Ca^{2+}]_i$ increase, we found that PTX pretreatment of dHL60 cells completely inhibited the peptide-induced calcium increase, however, PTX partially inhibited the calcium signaling stimulated by P18 or P24 in undifferentiated HL60 cells (data not shown). These results suggest that the receptors of peptides in dHL60 cells are coupled to PTX-sensitive G-proteins, and that the peptide receptors in undifferentiated HL60 cells might be coupled to PTX-insensitive G-proteins. These results indicate that the receptors of the peptides in undifferentiated HL60 cells are not the same as those in dHL60 cells.

Figure 9:
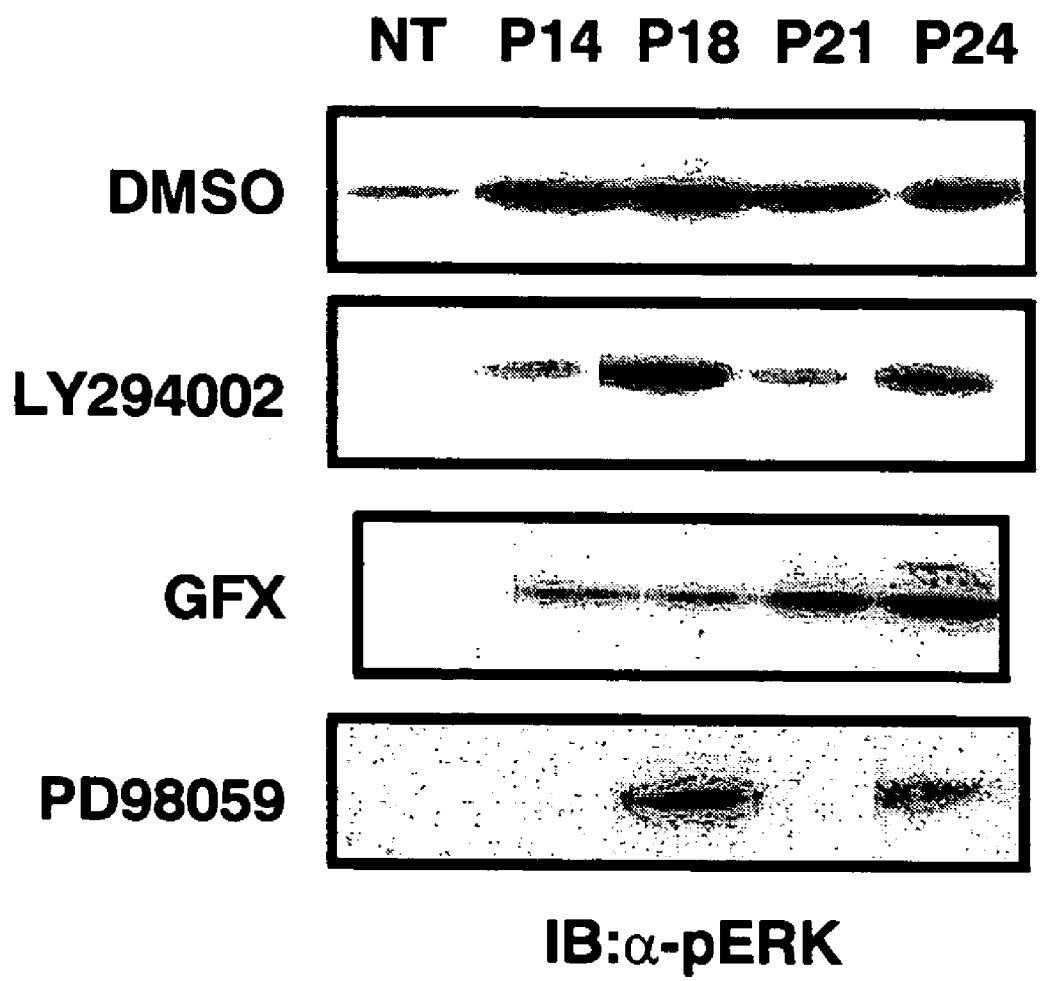
FIG. 9 shows regulation of each peptide-stimulated ERK phosphorylation in dHL60 cells. dHL60 cells were preincubated with vehicle or 10 µM of LY294002, 5 µM of GFX, or 50 µM of PD98059 for 15 min prior to treatment with 10 µM of each peptide or vehicle alone for 2 min. Each sample (30 µg of protein) was subjected to 8% SDS-PAGE, and phosphorylated ERK was quantified by immunoblot analysis with anti-phospho-ERK antibody. The results shown are from a single experiment representative of at least three independent experiments.

Through the study of intracellular signaling pathways by the inventive peptides, we demonstrated that P14 induced ERK activation via PI3K and PKC, and that P18 induced ERK activation via PKC (FIG. 9). In terms of the role of MEK, the 3 peptides, but not P18, caused ERK activation in a MEK-dependent manner (FIG. 9). FIG. 7 shows that 4 peptides stimulated $[Ca^{2+}]_i$ increase in FPRL1-expressing RBL-2H3 cells. Since dHL60 cells also express FPRL1, the 4 peptides may bind to FPRL1 in dHL60 cells. However, the observation that P18 induced ERK is PI3K- or MEK-independent suggests the involvement of another receptor in P18-mediated signaling. We found that P18 and P24 stimulated $[Ca^{2+}]_i$ increase in undifferentiated HL60 cells (FIG. 8). The results indicate that P14 and P21 bind to a receptor, such as FPRL1, and that P18 and P24 bind to at least two receptors, which include FPRL1 in leukocytic cells. In terms of the differential regulation of P18, P24, P14 or P21-induced ERK activation, it can be caused by different spectrum of receptors of the peptides.

Although chemoattractants are important immune-modulators and various chemoattractants (including chemokines) have been identified, applicants have for the first time identified a few short peptides acting on human leukocytes. fMLF is a well-known short chemotactic peptide, and has been useful for research on phagocyte activation (Pan et al. *J. Immunol.* 2000. 164: 404–411; He et al. *J. Immunol.* 2000. 165: 4598–4605). Because the inventive peptides stimulate human phagocytic cells, such as neutrophils and monocytes, these peptides can also be used as tools for the study of phagocytic cell functions. In the area of undifferentiated myeloma cell activation and signaling, no report has yet been issued on small peptides acting on undifferentiated myeloma cells. Because the inventive peptides stimulate undifferentiated HL60 cells, inducing a $[Ca^{2+}]_i$ increase, they are useful tools for the characterization of undifferentiated myeloma cell activation.

Peptides that Stimulate Target Cells

In one aspect, the invention is directed to any peptide that is capable of interacting with and activating target cells, preferably leukocytes and phagocytes. In particular, the peptide induces arachidonic acid, induces intracellular release of calcium and induces migration of the target cell.

It is understood that the inventive peptides may stimulate or activate a target cell such as leukocyte or phagocyte by any number of biochemical or enzymatic mechanisms, so long as the peptide activates the target cell. Polypeptides that activate target cells include without limitation the exemplified peptides, which include SEQ ID NO:1 to SEQ ID NO:35.

Nucleic Acid Encoding Polypeptide that Activates Target Cell

By "isolated" polynucleotide sequence, it is intended to encompass a nucleic acid molecule, DNA or RNA, which has been removed from its native environment. This includes segments of DNA encoding the inventive polypeptide and may further comprise heterologous sequences such as vector sequences or other foreign DNA. For example, recombinant DNA molecules contained in a vector are considered isolated for the purposes of the present invention, which may be partially or substantially purified.

In addition, isolated nucleic acid molecules of the invention include DNA molecules, which comprise a sequence substantially different from those described above but which, either due to the degeneracy of the genetic code or other variability, still encode the inventive polypeptide. Thus, it would be routine for one skilled in the art to generate the variants described above, for instance, to optimize codon expression or general function for a particular host.

Variant and Mutant Polynucleotides

The present invention further relates to variants of the nucleic acid molecules which encode proteins, analogs or derivatives of the target cell activator polypeptide. Such nucleic acid variants include those produced by nucleotide substitutions, deletions, or additions. The substitutions, deletions, or additions may involve one or more nucleotides. Alterations in the amino acid sequence may produce conservative or non-conservative amino acid substitutions, deletions or additions. Especially preferred among these are silent substitutions, additions and deletions, which do not alter the properties and activities of the polypeptides of the present invention or portions thereof. Also preferred in this regard are conservative substitutions.

The invention allows for the use of sequences in expression vectors, as well as to transfect host cells and cell lines, be these prokaryotic or eukaryotic cells. The invention also allows for purification of the polypeptides expressed from the expression vector. The expression vector may contain various molecular tags for easy purification. Subsequently obtained expression construct may be transformed into any host cell of choice. Cell lysates from the host cell is isolated by established methods well known in the field.

Variant and Mutant Polypeptides

To improve or alter the characteristics of the stimulator polypeptide, amino acid engineering may be employed. Recombinant DNA technology known to those skilled in the art can be used to create novel mutant polypeptides including single or multiple amino acid substitutions, deletions, additions, or fusion proteins. Such modified polypeptides can show, e.g., increased/decreased activity or increased/decreased stability. In addition, they may be purified in higher yields and show better solubility than the corresponding natural polypeptide, at least under certain purification and storage conditions.

Of special interest are substitutions of charged amino acids with other charged or neutral amino acids which may produce proteins with highly desirable improved characteristics, such as less aggregation of the produced polypeptides. Aggregation may not only reduce activity but may also be problematic when preparing pharmaceutical formulations, because aggregates can be immunogenic.

Antibodies

In one embodiment, the present invention is directed to detecting the activator polypeptide bound to the target cells using a variety of detection methods. One way to detect binding of the activating polypeptide to the target cells is to label the activator polypeptide directly and assay for its binding using labeling and separation techniques that are routine to a person of skill in the art. Other methods include using a labeled ligand that specifically binds to either the activator polypeptide or activator polypeptide/target cell complex. Such a ligand may be an antibody.

Purified activator polypeptide or activator polypeptide/target cell complex can be used to produce monoclonal or polyclonal antibody. Subsequently obtained monoclonal or polyclonal antibody can be used to determine the binding of the activator polypeptide to the target cell in various samples including cells, tissues, and body fluids such as but not limited to serum, plasma, and urine. Activator polypeptide or activator polypeptide/target cell complex may be assayed using a variety of molecular biological methods, which include but are not limited to in situ hybridization, immunoprecipitation, immunofluorescence staining, Western blot analysis and so on. One can carry out ELISA by using monoclonal antibody against activator polypeptide or activator polypeptide/target cell complex.

Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Labels

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur ($^{35}$S), tritium ($^{3}$H), indium ($^{112}$In), and technetium ($^{99}$Tc), and fluorescent labels, such as fluorescein and rhodamine, and biotin.

Examples of suitable enzyme labels include malate dehydrogenase, d-5-steroid isomerase, yeast-alcohol dehydrogenase, a-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is preferred isotope where in vivo imaging is used since its avoids the problem of dehalogenation of the $^{125}$I or $^{131}$I-labeled polypeptide by the liver. In addition, this radionucleotide has a more favorable gamma emission energy for imaging. For example, $^{111}$In coupled to monoclonal antibodies with 1-(P-isothiocyanatobenzyl)-DPTA has shown little uptake in non-tumors tissues, particularly the liver, and therefore enhances specificity of tumor localization.

Examples of suitable non-radioactive isotopic labels include $^{157}$Gd, $^{55}$Mn, $^{162}$Dy, $52^{Tr}$, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include, Pseudomonas toxin, diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron. Deuterium may also be used. Other contrasting agents also exist for EPR, PET or other imaging mechanisms, which are known to persons of skill in the art.

Typical techniques for binding the above-described labels to polypeptides are provided by Kennedy et al. (1976) Clin. Chim. Acta 70:1–31, and Schurs et al. (1977) Clin. Chim. Acta 81:1–40. Coupling techniques include the glutaraldehyde method, the periodate method, the dimaleimide method, the m-maleimidobenzyl-N-hydroxy-succinimide ester method, all of which methods are incorporated by reference herein.

Gene Therapy

In a specific embodiment, nucleic acids comprising sequences encoding the inventive polypeptide are administered to activate the target cell, such as leukocyte or phagocyte to enhance its immune response to bacteria or any other foreign substance by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

Therapeutic Composition

In one embodiment, the present invention relates to treatment for various conditions that are characterized by lack of sufficient target cell activation. In this way, the inventive therapeutic compound may be administered to human patients who are either suffering from, or prone to suffer from the disease or condition by providing compounds that stimulate target cell activation. Preferably, the target cell may be leukocyte or phagocyte. In particular, the disease or condition may be associated with infection by various infectious pathogens such as viruses or bacteria. Further in particular, the present invention is directed to treatment for an infectious disease accompanied by attenuation of normal immune response, such as acquired immune deficiency syndrome or cancer.

The formulation of therapeutic compounds is generally known in the art and reference can conveniently be made to Remington's Pharmaceutical Sciences, 17th ed., Mack Publishing Co., Easton, Pa., USA. For example, from about 0.05 µg to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (eg using slow release molecules by the intraperitoneal route or by using cells e.g. monocytes or dendrite cells sensitized in vitro and adoptively transferred to the recipient). Depending on the route of administration, the peptide may be required to be coated in a material to protect it from the action of enzymes, acids and other natural conditions which may inactivate said ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 µg/ml of carrier. In the case of compositions containing supplementary active ingredients, the dosages are determined by reference to the usual dose and manner of administration of the said ingredients.

Delivery Systems

Various delivery systems are known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody or a peptide of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, i.e., the brain, thus requiring only a fraction of the systemic dose.

A composition is said to be "pharmacologically or physiologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Materials and Methods

Fmoc amino acids were obtained from Millipore (Bedford, Mass.), Rapidamide resin from Dupont (Boston, Mass.), peripheral blood mononuclear cell (PBMC) separation medium (Histopaque-1077), cytochrome c, and fMLF from Sigma (St. Louis, Mo.), fura-2 pentaacetoxymethylester (fura-2/AM) from Molecular Probes (Eugene, Oreg.), RPMI 1640 from Life Technologies (Grand Island, N.Y.), dialyzed fetal bovine serum and supplemented bovine serum from Hyclone Laboratories Inc. (Logen, Utah), pertussis toxin (PTX), GF109203X, and PD98059 from Calbiochem (San Diego, Calif.), and LY294002 was purchased from BIOMOL Research Laboratories, Inc. (Polymouth Meeting, Pa.).

Example 2

Cell Culture and HL60 Cell Differentiation

U937 (human histiocytic lymphoma cells), HL60 (human promyelocytic leukemia cells), Raw 264.7 (mouse macrophage), Jurkat (human acute T cell leukemia), PC12 (rat adrenal pheochromocytoma cells), 3Y1 (Rat embryonic fibroblasts), 3T3L1 (preadipocytes), and NCI-H292 (human mucoepidermoid pulmonary carcinoma cells) were obtained from the American Type Culture Collection (Rockville, Md.) and maintained as recommended. FPR- or FPRL1 expressing RBL-2H3 cells were cultured as described previously (He et al. *J. Immunol.* 2000. 165: 4598–4605). Cells were maintained at about $1\times10^6$ cells/ml under standard incubator conditions (humidified atmosphere, 95% air, 5% $CO_2$, at 37° C.). HL60 cells were induced to differentiate into the granulocyte phenotype by adding dimethylsulfoxide (DMSO) (final concentration 1.25%, v/v) for 4 days to the culture medium, as described previously (Itoh et al. *Blood.* 1998. 92: 1432–1441).

Example 3

Isolation of Leukocytes

Peripheral blood leukocyte concentrates were donated by the Ulsan Red Cross Blood Center (Ulsan, Korea). PBMCs were separated on a Histopaque-1077 gradient. After two washings with HBSS without $Ca^{2+}$ and $Mg^{2+}$, the PBMCs were suspended in 10% FBS containing RPMI and incubated for 60 min at 37° C. to let the monocytes attach to the culture dish. Cells were washed 5 times with warmed RPMI medium to remove lymphocytes, and then the attached monocytes were collected, as described previously (Bae et al. *J. Leukoc. Biol.* 1999. 65: 241–248). Human neutrophils were isolated according to standard procedures; i.e., dextran sedimentation, hypotonic lysis of erythrocytes, and using a medium lymphocyte separation gradient, as described previously (Seo et al. *J. Immunol.* 1997. 158: 1895–1901). Isolated human leukocytes were then used promptly.

Example 4

Preparation of Peptide Libraries, and the Synthesis and Analysis of Peptides

The hexapeptide libraries were prepared in the Peptide Library Support Facility of Pohang University of Science and Technology, as described previously (Baek et al., *J. Biol. Chem.* 1996. 271: 8170–8175, incorporated by reference herein in its entirety). Finally, 114 peptide pools (Cys was excluded from the library constructions) were individually dissolved in water to a final concentration of 27 nM per peptide. The peptides were synthesized by the solid-phase method described previously (Baek et al. *J. Biol. Chem.* 1996. 271: 8170–8175). Briefly, peptides were synthesized on a Rapidamide support resin and assembled following the standard Fmoc/t-butyl strategy on an acid-labile linker. The composition of peptides was confirmed by amino acid analysis, as described previously (Baek et al. *J. Biol. Chem.* 1996. 271: 8170–8175).

Example 5

Initial Screening of the PS-SPCLs and the Measurement of AA Release

For the initial screening of the PS-SPCLs, we measured the AA release stimulating activity of each peptide pool. Cultured dHL60 cells ($10^7$ cells/ml) were pre-labeled with 0.5 µCi/ml of ($^3$H)-AA in RPMI 1640 medium containing 10% FBS for 90 min at 37° C. in a humidified incubator supplied with 95% air and 5% $CO_2$, as described previously (Bae et al. *J. Immunol.* 2000. 164: 4089–4096). The labeled cells were then washed twice with serum-free RPMI 1640 and incubated in RPMI 1640 medium containing 0.1% fatty acid-free BSA for 15 min at 37° C. After discarding the medium, the cells were stimulated with various concentrations of peptide for the indicated times. Radioactivity in the medium and of collected cells was determined with a liquid scintillation counter. When investigating the effects of inhibitors, cells were preincubated with the indicated concentrations of each inhibitor or vehicle for 15 min prior to stimulation.

Example 6

Measurement of $[Ca^{2+}]_i$

The level of $[Ca^{2+}]_i$ was determined using Grynkiewicz's method using fura-2/AM (Grynkiewicz et al. *J. Biol. Chem.* 1985. 260: 3440–3550). Briefly, prepared cells were incubated with 3 µM of fura-2/AM at 37° C. for 50 min in serum-free RPMI 1640 medium under continuous stirring. $2 \times 10^6$ cells were aliquoted for each assay in $Ca^{2+}$ free Locke's solution (154 mM NaCl, 5.6 mM KCl, 1.2 mM $MgCl_2$, 5 mM HEPES, pH 7.3, 10 mM glucose, and 0.2 mM EGTA). Fluorescence changes were measured at the dual excitation wavelength of 340 nm and 380 nm, and the calculated fluorescence ratio was translated into $[Ca^{2+}]_i$.

Example 7

Measurement of Superoxide Generation

We determined superoxide anion generation by measuring cytochrome c reduction using a microtiter 96 well plate ELISA reader (Bio-Tekinstruments, EL312e, Winooski, Vt.) as described previously (Bae et al. *Blood.* 2001. 97: 2854–2862). Human neutrophils ($1 \times 10^6$ cells/100 µl of RPMI 1640 medium per well of a 96-well plate) were preincubated with 50 µM of cytochrome c at 37° C. for 1 min and then incubated with the indicated peptide concentrations. Superoxide generation was determined from change in light absorption at 550 nm over 5 minutes at 1 min intervals.

Example 8

Chemotaxis Assay

Chemotaxis assays were performed using multiwell chambers (Neuroprobe Inc., Gaithersburg, Md.) (Bae et al. *Blood.* 2001. 97: 2854–2862). Briefly, prepared human monocytes were suspended in RPMI at a concentration of $1 \times 10^6$ cells/ml, and 25 µl of the suspension was then placed onto the upper well of a chamber separated by a 5 µm polyhydrocarbon filter (3 µm pores size not polyvinylpyrrolidone coated, as is needed for neutrophils) from peptides or N-formyl-methionyl-leucyl-phenylalanine (fMLF) in the lower well. After incubation for 2 hours (90 minutes for neutrophils) at 37° C., non-migrated cells were removed by scraping, and cells that migrated across the filter were dehydrated, fixed, and stained with hematoxylin (Sigma, St. Louis, Mo.). Stained cells were counted in five randomly chosen high power fields (HPF) (400×) (Bae et al. *Blood.* 2001. 97: 2854–2862).

Example 9

Results

Example 9.1

Identification of Peptides that Stimulate AA Release in dHL60 Cells

We screened 114 peptide pools (around 47 million different peptides) from hexapeptide PS-SPCLs to identify those peptides that stimulate AA release in dHL60 cells. FIG. 1 shows the results of the initial screening. Amino acids in different positions of the hexapeptides induced different levels of AA release stimulating activity. The most active peptide/position combinations were peptides having the formula XKXXXM (SEQ ID NO:1), wherein Lys (K), Met (M), or Arg (R) are in the first position, Lys (K) in second, His (H), Lys (K), or Tyr (Y) in third, His (H), Lys (K), or Tyr (Y) in fourth, Lys (K), Pro (P), Arg (R), Val (V), or Tyr (Y) in fifth, and Met (M) in sixth.

Figure 2:
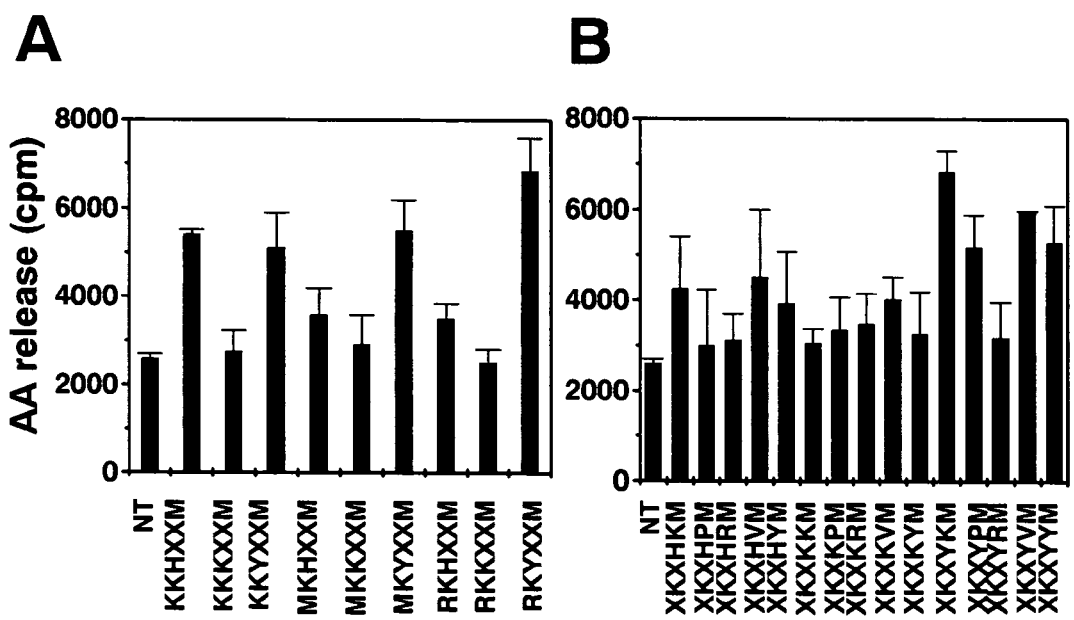
FIGS. 2A and 2B show effects of several candidate peptides synthesized on the basis of the screening results of the PS-SPCLs with respect to AA release in dHL60 cells. ($^3$H) AA-labeled differentiated HL60 cells were stimulated with 1 µM concentrations of several peptides or 1 µM fMLF, and AA release was measured. The results are presented as means ±S.E. of three independent experiments. * $P<0.01$ versus vehicle treatment.

Based on the results of the first screening of the peptide libraries, we generated by reiterative synthesis peptide pools containing $1 \times 1 \times 1 \times 3 \times 5 \times 1 = 15$ or $3 \times 1 \times 3 \times 1 \times 1 \times 1 = 9$ individual hexapeptides. We then tested the effectiveness of these peptide pools for AA release stimulating activity in dHL60 cells using the same methods as used in the initial screening (FIGS. 2A and 2B). After this second screening, we found that KKHXXX (SEQ ID NO:2), KKYXXX (SEQ ID NO:3), RKYXXX (SEQ ID NO:4), MKYXXX (SEQ ID NO:5), XXXHKM (SEQ ID NO:6), XXXHVM (SEQ ID NO:7), XXXYKM (SEQ ID NO:8), XXXYPM (SEQ ID NO:9), XXXYVM (SEQ ID NO:10), or XXXYYM (SEQ ID NO:11) were most active (FIGS. 2A and 2B). Finally, 24 different synthesized peptides are listed in Table I and measured for their effect on AA release in dHL60 cells. All of these 24 peptides stimulated AA release at a concentration of 10 µM (Table I), and (K/R/M)KYY(P/V/Y)M (P10, P11, P12, P16, P17, P18, P22, P23, and P24), (R/M)KYHVM (P14, P20) and MKYYKM (P21) were the most potent (Table I).

TABLE I

Effect of inventive peptides on arachidonic acid release in differentiated HL60 cells[a]

| Peptide | Sequence | Folds of increase (% of total) |
|---|---|---|
| P1 | KKHHKM-NH$_2$ (SEQ ID NO:12) | 1.25 ± 0.168 |
| P2 | KKHHVM-NH$_2$ (SEQ ID NO:13) | 1.23 ± 0.153 |
| P3 | KKHYKM-NH$_2$ (SEQ ID NO:14) | 1.45 ± 0.306 |
| P4 | KKHYPM-NH$_2$ (SEQ ID NO:15) | 1.41 ± 0.247 |
| P5 | KKHYVM-NH$_2$ (SEQ ID NO:16) | 1.68 ± 0.390 |
| P6 | KKHYYM-NH$_2$ (SEQ ID NO:17) | 1.52 ± 0.296 |
| P7 | KKYHKM-NH$_2$ (SEQ ID NO:18) | 1.42 ± 0.226 |
| P8 | KKYHVM-NH$_2$ (SEQ ID NO:19) | 1.30 ± 0.170 |
| P9 | KKYYKM-NH$_2$ (SEQ ID NO:20) | 1.49 ± 0.268 |
| P10 | KKYYPM-NH$_2$ (SEQ ID NO:21) | 2.27 ± 0.199 |
| P11 | KKYYVM-NH$_2$ (SEQ ID NO:22) | 2.49 ± 0.023 |
| P12 | KKYYYM-NH$_2$ (SEQ ID NO:23) | 2.58 ± 0.168 |
| P13 | RKYHKM-NH$_2$ (SEQ ID NO:24) | 1.47 ± 0.220 |
| P14 | RKYHVM-NH$_2$ (SEQ ID NO:25) | 2.23 ± 0.403 |
| P15 | RKYYKM-NH$_2$ (SEQ ID NO:26) | 1.71 ± 0.214 |
| P16 | RKYYPM-NH$_2$ (SEQ ID NO:27) | 2.57 ± 0.450 |
| P17 | RKYYVM-NH$_2$ (SEQ ID NO:28) | 2.82 ± 0.210 |
| P18 | RKYYYM-NH$_2$ (SEQ ID NO:29) | 2.61 ± 0.295 |
| P19 | MKYHKM-NH$_2$ (SEQ ID NO:30) | 1.68 ± 0.221 |
| P20 | MKYHVM-NH$_2$ (SEQ ID NO:31) | 2.55 ± 0.271 |

TABLE I-continued

Effect of inventive peptides on arachidonic acid release in differentiated HL60 cells[a]

| Peptide | Sequence | Folds of increase (% of total) |
|---|---|---|
| P21 | MKYYKM-NH$_2$ (SEQ ID NO:32) | 2.86 ± 0.426 |
| P22 | MKYYPM-NH$_2$ (SEQ ID NO:33) | 2.95 ± 0.668 |
| P23 | MKYYVM-NH$_2$ (SEQ ID NO:34) | 3.05 ± 0.401 |
| P24 | MKYYYM-NH$_2$ (SEQ ID NO:35) | 2.93 ± 0.323 |

[a]Arachidonic acid release was measured in [$^3$H] arachidonic acid-labeled cells stimulated with 10 µM of peptide.

Example 9.2

Figure 3:
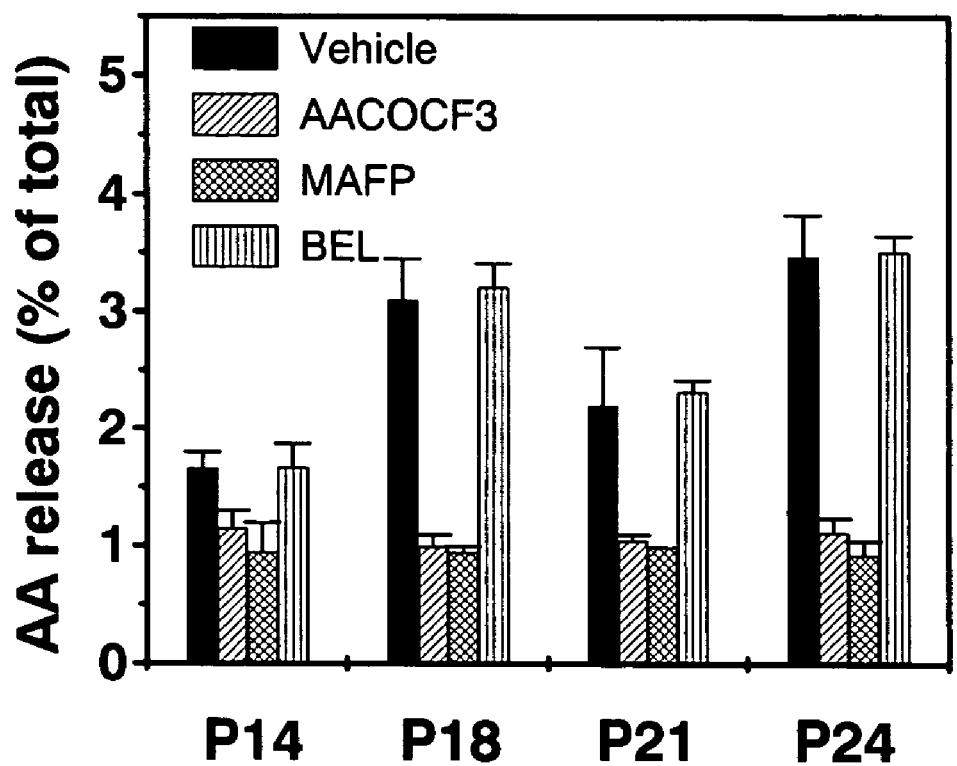
FIG. 3 shows peptide-induced AA release derived from $cPLA_2$ activation. dHL60 cells were suspended in HBSS containing 0.1% fatty acid-free BSA, incubated for 15 min in the presence or absence of 10 µM of MAFP, $AACOCF_3$, and BEL at 37° C., and stimulated for 30 min with 1 µM of each peptide or vehicle as control. Release of ($^3$H)-arachidonic acid into the extracellular medium was determined with a liquid scintillation counter. Results are expressed as percentages of total cellular radioactivity, mean values ±S.E. (n=6) are shown.

Effect of Isozyme-Specific Inhibitors of PLA$_2$ on the Peptide-Stimulated AA Release To address the question as to which isoform of PLA$_2$ is responsible for peptide-induced AA release, several isoform-specific inhibitors of PLA$_2$ were added together with several representative peptides, and were found to stimulate AA release at 1 µM in dHL60 cells (FIG. 3). Pretreatment of these cells with the cPLA$_2$-specific inhibitors, AACOCF$_3$ and MAFP blocked the induction of AA by 4 of the peptides, P14, P18, P21, and P24 (FIG. 3). 10 µM of MAFP or AACOCF$_3$ almost completely prevented AA release as induced by the 4 peptides, whereas another PLA$_2$ inhibitor, BEL, known to be specific for iPLA$_2$, did not interfere with peptide-induced AA release (FIG. 3). AA stimulated release by these peptides was also inhibited by the chelation of intracellular Ca$^{2+}$ with BAPTA/AM, which also supports the notion of cPLA$_2$ activation (data not shown). These results, therefore, indicate that the 4 peptides evoke AA release by stimulating cPLA$_2$ but not iPLA$_2$ in dHL60 cells.

Example 9.3

Effect of Peptides on [Ca$^{2+}$]$_i$ Rise in dHL60 Cells

Figure 4:
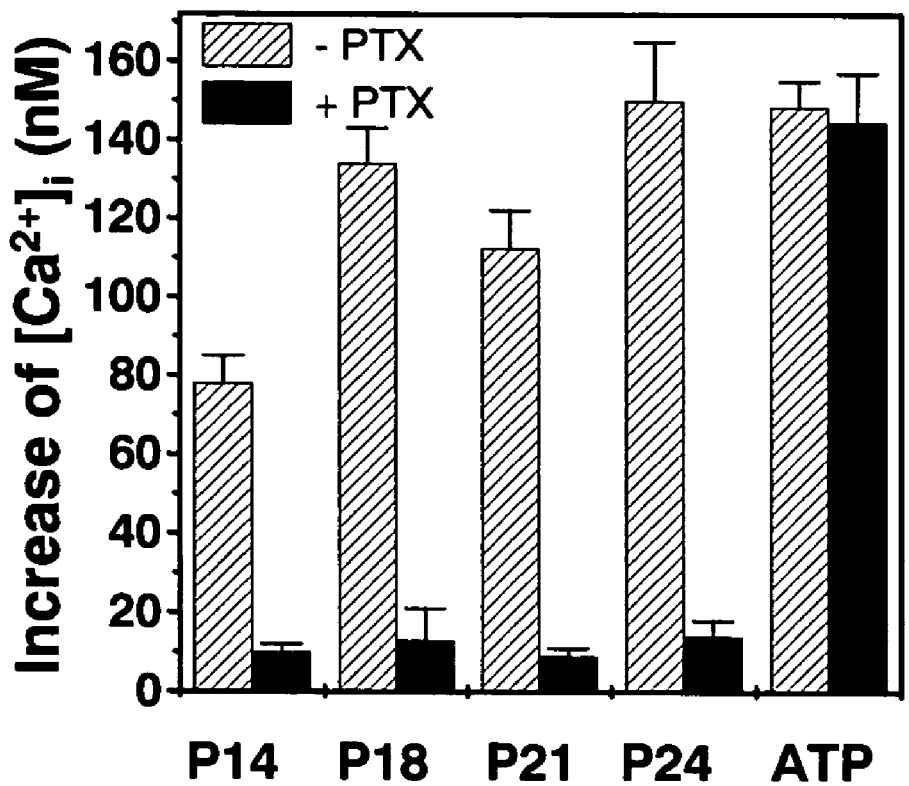
FIG. 4 shows effect of PTX on peptide-induced $[Ca^{2+}]_i$ rise in dHL60 cells. dHL60 cells were incubated in the presence or absence of PTX (150 ng/ml) for 20 hr and the cells were loaded with fura-2. The fura-2-loaded dHL60 cells were stimulated with 1 µM of each peptide or 500 µM of ATP. The change in 340/380 nm was monitored. Results are representative of 4 independent experiments. Data are presented as means ±S.E. of four independent experiments.

It is well known that intracellular calcium elevation is essentially required for the activation of cPLA$_2$ (Gijon et al. J. Leukoc. Biol. 1999. 65: 330–336). The finding that peptide-stimulated AA release is inhibited by preincubating dHL60 cells with a cPLA$_2$ inhibitor, MAFP, led us to investigate whether the peptides affect [Ca$^{2+}$]$_i$ increase. As shown in Table II, many of the peptides caused an increase in [Ca$^{2+}$]$_i$ after stimulation at 1 µM in dHL60 cells, though some peptides, like P1 and P7 did not affect [Ca$^{2+}$]$_i$ increase (Table II). The concentration dependency of the peptide-induced [Ca$^{2+}$]$_i$ increase was also investigated. P3, P4, P5, and P6 showed maximal activity at concentrations exceeding 20 µM (data not shown), P10, P11, P12, P16, P17, P18, P22, P23, and P24 showed maximal activity at approximately 3 µM (data not shown). A number of reports have demonstrated that many extracellular ligands modulate cellular activities via PTX-sensitive G-protein(s) in human leukocytic cells (Sano et al. J. Immunol. 2000. 165: 2156–2164; Badolato et al. J. Immunol. 1995. 155: 4004–4010). To investigate the possible involvement of PTX-sensitive G-protein in peptide-induced [Ca$^{2+}$]$_i$ increases, dHL60 cells were treated with PTX (150 ng/ml) for 20 hr prior to the addition of each of the 24 peptides. As shown in FIG. 4, each active peptide-induced [Ca 2+]$_i$ rise was almost completely inhibited by PTX. ATP, a ligand that does not act on PTX-sensitive G-protein-coupled receptors, stimulated [Ca$^{2+}$]$_i$ increases in dHL60 cells and this [Ca$^{2+}$]$_i$ rise was not inhibited by PTX (FIG. 4). These results indicate that the peptides stimulate [Ca$^{2+}$]$_i$ release via PTX-sensitive G-protein in dHL60 cells.

TABLE II

Effect of inventive peptides on intracellular calcium increase in differentiated HL60 cells[b]

| Peptide | [Ca$^{2+}$]$_i$ (nM) |
|---|---|
| P1 | 0 |
| P2 | 0 |
| P3 | 8 ± 3.2 |
| P4 | 14 ± 4.1 |
| P5 | 34 ± 9.5 |
| P6 | 50 ± 11.7 |
| P7 | 0 |
| P8 | 31 ± 3.5 |
| P9 | 85 ± 15.8 |
| P10 | 152 ± 28.7 |
| P11 | 158 ± 25.3 |
| P12 | 153 ± 13.2 |
| P13 | 10 ± 4.2 |
| P14 | 85 ± 9.5 |
| P15 | 77 ± 12.1 |
| P16 | 135 ± 21.4 |
| P17 | 143 ± 10.2 |
| P18 | 150 ± 14.5 |
| P19 | 13 ± 3.0 |
| P20 | 155 ± 16.3 |
| P21 | 122 ± 15.7 |
| P22 | 168 ± 21.6 |
| P23 | 153 ± 13.2 |
| P24 | 165 ± 23.4 |

[b]Intracellular calcium increase was monitored in fura-2 loaded cells stimulated with 1 µM of peptide.

Example 9.4

Cell Type Specificity of the Peptides

Figure 5:
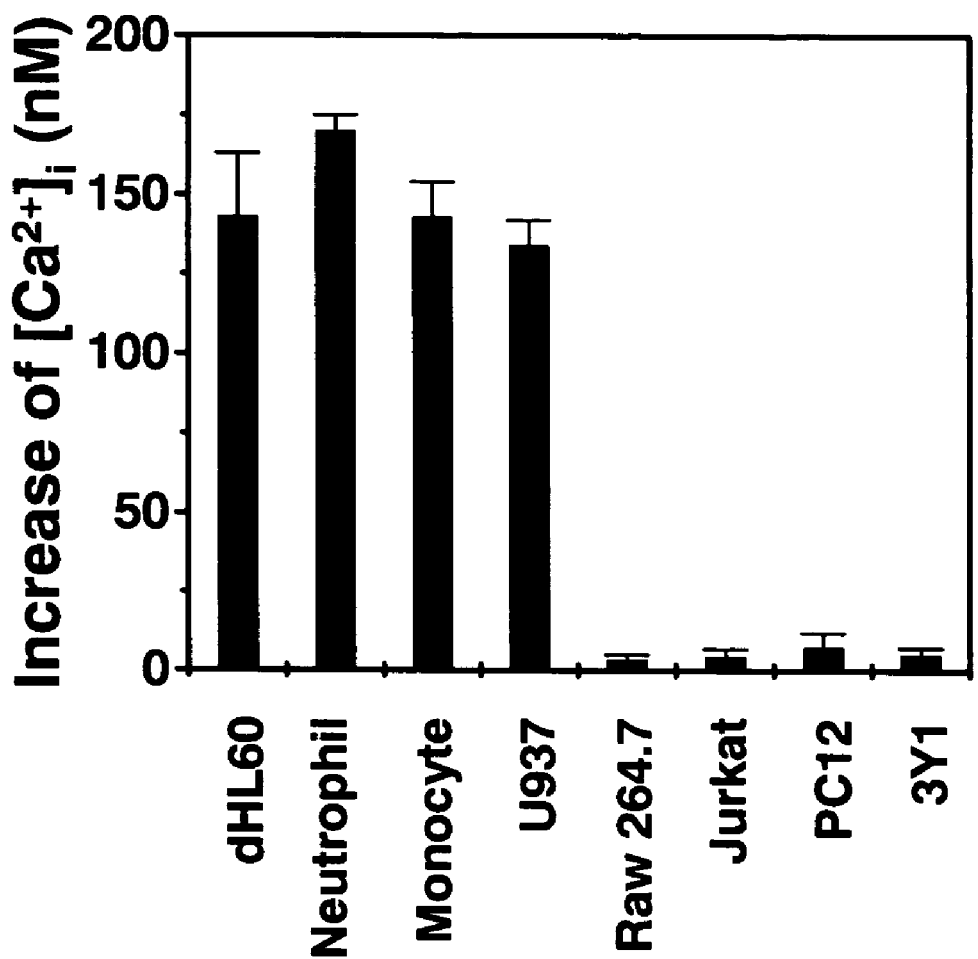
FIG. 5 shows effect of P24 on $[Ca^{2+}]_i$ rise in cells of various origins. Each cell was loaded with fura-2 for 50 minutes. The cells were stimulated with 10 µM and $[Ca^{2+}]_i$ increase was monitored. Data are presented as means ±S.E. of three independent experiments.

Since the synthesized peptides stimulated neutrophil-like dHL60 cells, we checked their effects on neutrophils, a type of leukocyte. The stimulation of neutrophils with one of the peptides, P24, resulted in a [Ca$^{2+}$]$_i$ rise (FIG. 5). Monocytes and U937 cells were also activated by P24 (FIG. 5), but Raw 264.7 and Jurkat cells were not activated by P24 (FIG. 5). Next, we examined the effects of P24 on [Ca$^{2+}$]$_i$ rise in several non-leukocytic cell lines. However, 3Y1, PC12, NCI-H292, and HUVEC cell lines showed no response to P24 in terms of [Ca$^{2+}$]$_i$ rise (FIG. 5 and data not shown). These results indicate that the peptide effects are neutrophil and monocyte specific. The other active peptides showed similar results in terms of their leukocyte-specificities (data not shown).

Example 9.5

Effect of the Peptides on Superoxide Generation

Superoxide generation is one of the important steps in the host's defense mechanism by phagocytes (Lambeth et al. J. Bioenerg. Biomembr. 1988. 20: 709–733). We tested the effect of the 4 representative peptides (P14, P17, P21, and P24) on superoxide generation in human neutrophils. These 4 peptides were found to stimulate superoxide generation in a concentration-dependent manner in human neutrophils (data not shown). Moreover, the stimulation of human neutrophils with 1 µM of each peptide caused a dramatic change in superoxide generation (Table III). P24 was the most potent in terms of superoxide generation in human neutrophils (Table III).

TABLE III

Effect of peptides on superoxide generation in human neutrophils[c]

| Peptide | Superoxide production (nmole/$10^6$ cells) |
|---|---|
| P14 | 9.3 ± 1.42 |
| P18 | 28.4 ± 3.21 |
| P21 | 12.7 ± 1.76 |
| P24 | 34.2 ± 0.48 |
| fMLF | 26.5 ± 1.32 |

[c]Superoxide production was measured by monitoring the amount of cytochrome c reduction caused by stimulating with 1 µM of peptide.

Example 9.6

Chemotactic Effect of Peptides on Leukocytes

Figure 6:
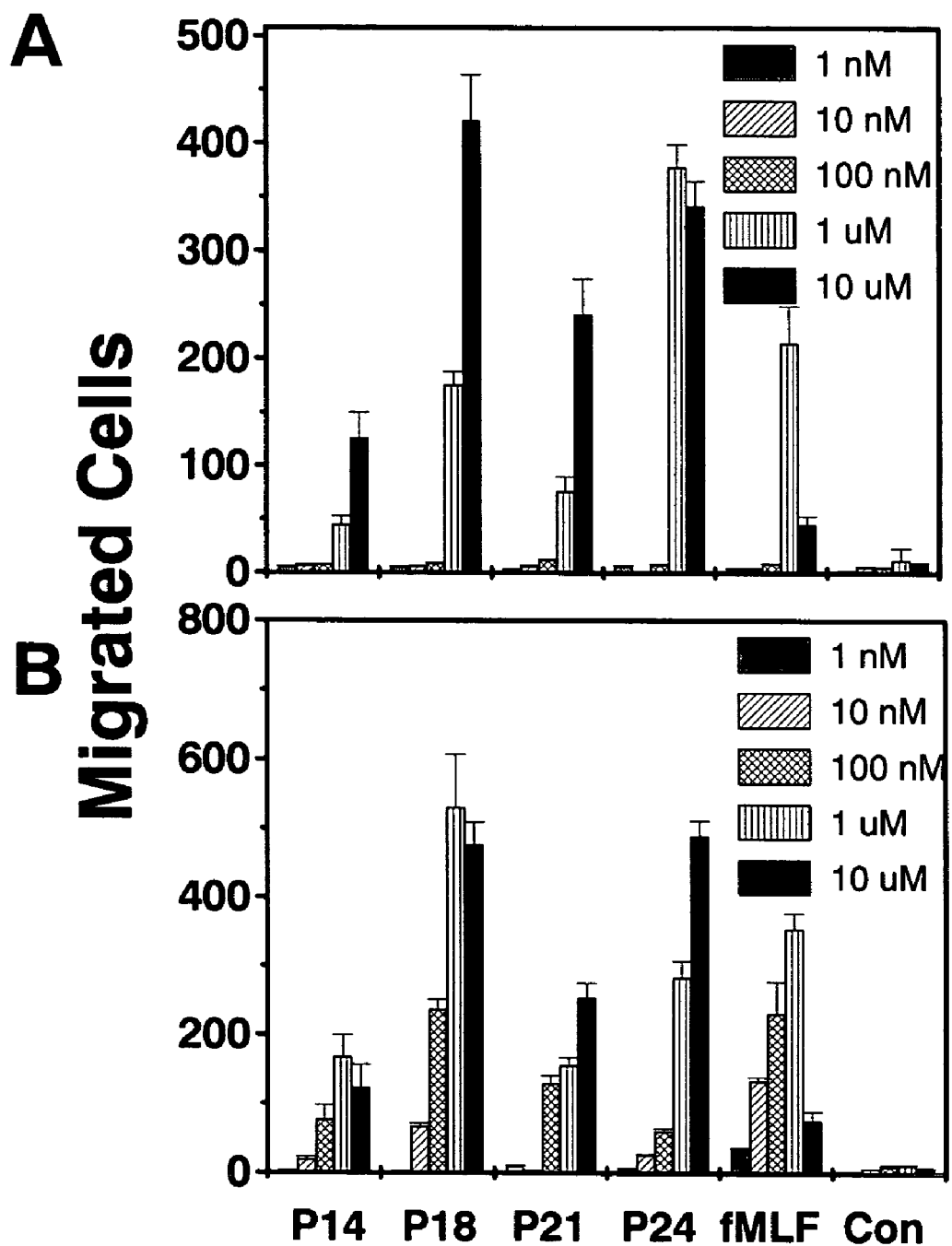
FIGS. 6A and 6B show chemotactic effect of peptides. Assays were performed using a modified Boyden chamber assay, as described in the Examples. Isolated human neutrophils (A) or monocytes (B) ($1 \times 10^6$ cells/ml in serum free RPMI) were added to the upper wells of a 96-well chemotaxis chamber and migration across a 3 µm pore size (5 µm for monocytes) polycarbonate membrane was assessed after 2 hrs incubation at 37° C. The numbers of migrated cells were determined by counting them in a high power field (400×). Results are presented as means ±S.E. of three independent experiments each performed in duplicate.

We found that 4 peptides (P14, P18, P21, and P24) stimulated superoxide generation and $[Ca^{2+}]_i$ increase in human phagocytic cells. These peptide-induced phagocyte activation phenomena are similar to chemoattractant-induced phenomena. Therefore, we checked whether the peptides exhibited chemotactic activity on human monocytes or neutrophils. The 4 active peptides induced migration of human neutrophils over a concentration range of 1–10 µM (FIG. 6A). The maximal cellular migration-inducing activity mediated by the peptides was more than 200% of that induced by 1 µM of fMLF (FIG. 6A). The 4 peptides (P14, P17, P21, and P24) also induced cellular chemotaxis in human monocytes (FIG. 6B). Moreover, the 4 peptides caused monocyte chemotaxis in a concentration range of 0.01 to 10 µM (FIG. 6B). An inactive control peptide, LFMYHP (SEQ ID NO:36), did not induce cellular chemotaxis in neutrophils or monocytes at concentrations less than 10 µM (FIGS. 6A and 6B). In four experiments with independently prepared leukocytes, the 4 peptides showed similar cellular migration-inducing activity.

Example 9.7

Receptor Specificity of the Peptides: Effect on FPRL1

Peptide induced phagocyte activation was found to be very similar to that induced by chemoattractants. Formyl peptide receptor, FPR, and FPRL1 are well-known chemoattractant receptors in neutrophils (Le et al. *Immunol. Rev.* 2000. 177: 185–194; Le et al. *Cytokine Growth Factor Rev.* 2001. 12: 91–105). To examine whether the peptides bind to FPR or FPRL1 we investigated the effect of the peptides on $[Ca^{2+}]_i$ increase in FPR- or FPRL1-expressing RBL-2H3 cells. No peptide was found to affect $[Ca^{2+}]_i$ in FPR-expressing RBL-2H3 cells (data not shown). However, several peptides including 4 peptides (P14, P18, P21, and P24) induced calcium increase in FPRL1-expressing RBL-2H3 cells (FIG. 7 and data not shown). An inactive control peptide (LFMYHP (SEQ ID NO:36)) was found not to be able to induce calcium increase in FPRL1 cells (FIG. 7). Among the active peptides, the potency of calcium increasing activities was found to be different for each peptide. These results indicate that several peptides, including the 4 peptides (P14, P18, P21, and P24) are ligands for FPRL1 but not for FPR.

Example 9.8

Differentiation Status Specificity of the 4 Peptides in HL60 Cells

FIG. 5 shows that the peptides acted on leukocytic cells but not on non-leukocytic cells. Many extracellular ligands have been reported to have cellular differentiation status specificity (Rabin et al. *J. Immunol.* 1999. 162: 3840–3850; Berardi et al. *Blood.* 1995. 86: 2123–2129). We investigated whether the peptides showed such differentiation status specificity in myelocytes, by checking the effect of these peptides on $[Ca^{2+}]_i$ increase in undifferentiated and differentiated HL60 cells. As shown in Table II, the 4 peptides stimulated $[Ca^{2+}]_i$ increase in dHL60 cells. When undifferentiated HL60 cells were stimulated with the 4 peptides, $[Ca^{2+}]_i$ was found to be dramatically induced by P18 and P24 (FIG. 8). The other 2 peptides, P14 and P21, did not affect $[Ca^{2+}]_i$ increase in HL60 cells (FIG. 8). Unlike neutrophils or dHL60 cells, undifferentiated HL60 cells do not express FPR or FPRL1 on the cell surface (Prossnitz et al. *J. Immunol.* 1993. 151: 5704–5715). We also confirmed that fMLF (a FPR-specific ligand) or lipoxin A4 (a FPRL1-specific ligand) did not affect $[Ca^{2+}]_i$ increase in HL60 cells, indicating that HL60 cells do not express FPR or FPRL1. These results suggest that receptors other than FPRL1 are activated by the peptides P18 and P24. Moreover, P14 and P21 stimulated dHL60 cells and FPRL1-expressing RBL-2H3 cells, demonstrating that 2 peptides show differentiation status specificity.

Example 9.9

Comparison of Intracellular Signaling by the 4 Peptides

Extracellular signal regulated protein kinase (ERK) is a well-known intracellular enzyme that mediates diverse cellular responses (Sugden et al. *Cell Signal* 1997. 9: 337–351). Many reports have demonstrated that chemoattractants stimulate ERK activity, and that this may result in several pivotal stages in the modulation of leukocytic cells (Woo et al. *J. Biol. Chem.* 2002. 277: 8572–8578; Brill et al. *J. Immunol.* 2001. 166: 7121–7127). In the present study, we found that the stimulation of dHL60 cells with 4 peptides (P14, P18, P21, and P24) caused a dramatic increase in the phosphorylation level of ERK (FIG. 9). Moreover, these peptide-induced ERK activation was time-dependent, and showed maximal activity 5 minutes after stimulation (data not shown). To compare the intracellular signaling involving these 4 peptides, dHL60 cells were pretreated either with LY294002 (50 µM), GF109203X (5 µM), or PD98059 (50 µM) or left untreated as a control. After being incubated for the indicated periods (15 minutes for LY294002 and GF109203X, 60 minutes for PD98059), the cells were stimulated with 1 µM of each peptide for 5 minutes. As shown in FIG. 9, P14-induced ERK phosphorylation was blocked by LY294002, GF109203X, or PD98059, indicating that the peptide-induced ERK activation is phosphatidylinositol-3-kinase (PI-3K), protein kinase C (PKC), or MEK-dependent. P18-induced ERK phosphorylation was completely blocked by GF109203X but not by LY294002 (FIG. 9). PD98059 partially blocked P18-induced ERK phosphorylation (FIG. 9). P21 also caused ERK phosphorylation showing P13K and MEK-dependency (FIG. 9), and P24-induced ERK phosphorylation was partially blocked by LY294002 but not by GF109203X (FIG. 9). These results suggest that the 4 peptides stimulate overlapping and non-overlapping intracellular signaling pathways, which result in the activation of ERK in dHL60 cells.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A polypeptide, which is about 4 to 20 amino acids in length, and which comprises SEQ ID NO:30, SEQ ID NO:31, SEQ ID NO:32, SEQ ID NO:33, SEQ ID NO:34, or SEQ ID NO:35.

2. The polypeptide according to claim 1, which is about 4 to 15 amino acids long.

3. The polypeptide according to claim 2, which is about 4 to 10 amino acids long.

4. The polypeptide according to claim 3, which is about 4 to 7 amino acids long.

5. The polypeptide according to claim 4, which is about 6 amino acids long.

6. A method of inducing expression of arachidonic acid in a target cell comprising contacting the target cell with the polypeptide of claim 1.

7. The method according to claim 6, wherein the target cell is a leukocyte or phagocyte.

8. A method of activating $PLA_2$ in a target cell comprising contacting the cell with the polypeptide according to claim 1.

9. The method according to claim 8, wherein the $PLA_2$ is c $PLA_2$.

10. The method according to claim 8, wherein the target cell is a leukocyte or phagocyte.

11. A method of producing superoxide in a target cell comprising contacting the cell with the polypeptide according to claim 1.

12. The method according to claim 11, wherein the target cell is leukocyte or phagocyte.

13. A method of causing movement of a target cell, comprising contacting the cell with a polypeptide according to claim 1.

14. The method according to claim 13, wherein the target cell expresses FPRL1.

15. The method according to claim 14, wherein the target cell does not express FPR.

* * * * *

SEQUENCE LISTING

```
<160> NUMBER OF SEQ ID NOS: 36

<210> SEQ ID NO 1
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be Lys, Met, or Arg
<220> FEATURE:
<221> NAME/KEY: MISC_FEATURE
<222> LOCATION: (3)..(3)
<223> OTHER INFORMATION: Xaa can be His, Lys, or Tyr
<220> FEATURE:
<221> NAME/KEY: MISC_FEATURE
<222> LOCATION: (4)..(4)
<223> OTHER INFORMATION: Xaa can be His, Lys, or Tyr
<220> FEATURE:
<221> NAME/KEY: MISC_FEATURE
<222> LOCATION: (5)..(5)
<223> OTHER INFORMATION: Xaa can be Lys, Pro, Arg, Val, or Tyr

<400> SEQUENCE: 1

Xaa Lys Xaa Xaa Xaa Met
1               5

<210> SEQ ID NO 2
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa can be His, Lys, or Tyr.
<220> FEATURE:
<221> NAME/KEY: MISC_FEATURE
<222> LOCATION: (5)..(5)
<223> OTHER INFORMATION: Xaa can be Lys, Pro, Arg, Val, or Tyr.
<220> FEATURE:
<221> NAME/KEY: MISC_FEATURE
<222> LOCATION: (6)..(6)
<223> OTHER INFORMATION: Xaa can be Met.

<400> SEQUENCE: 2

Lys Lys His Xaa Xaa Xaa
1               5

<210> SEQ ID NO 3
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa can be His, Lys, or Tyr.
```

```
<220> FEATURE:
<221> NAME/KEY: MISC_FEATURE
<222> LOCATION: (5)..(5)
<223> OTHER INFORMATION: Xaa can be Lys, Pro, Arg, Val, or Tyr.
<220> FEATURE:
<221> NAME/KEY: MISC_FEATURE
<222> LOCATION: (6)..(6)
<223> OTHER INFORMATION: Xaa can be Met.

<400> SEQUENCE: 3

Lys Lys Tyr Xaa Xaa Xaa
1               5

<210> SEQ ID NO 4
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa can be His, Lys, or Tyr.
<220> FEATURE:
<221> NAME/KEY: MISC_FEATURE
<222> LOCATION: (5)..(5)
<223> OTHER INFORMATION: Xaa can be Lys, Pro, Arg, Val, or Tyr.
<220> FEATURE:
<221> NAME/KEY: MISC_FEATURE
<222> LOCATION: (6)..(6)
<223> OTHER INFORMATION: Xaa can be Met.

<400> SEQUENCE: 4

Arg Lys Tyr Xaa Xaa Xaa
1               5

<210> SEQ ID NO 5
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa can be His, Lys, or Tyr.
<220> FEATURE:
<221> NAME/KEY: MISC_FEATURE
<222> LOCATION: (5)..(5)
<223> OTHER INFORMATION: Xaa can be Lys, Pro, Arg, Val, or Tyr.
<220> FEATURE:
<221> NAME/KEY: MISC_FEATURE
<222> LOCATION: (6)..(6)
<223> OTHER INFORMATION: Xaa can be Met.

<400> SEQUENCE: 5

Met Lys Tyr Xaa Xaa Xaa
1               5

<210> SEQ ID NO 6
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be Lys, Met, or Arg.
<220> FEATURE:
<221> NAME/KEY: MISC_FEATURE
<222> LOCATION: (2)..(2)
<223> OTHER INFORMATION: Xaa can be Lys.
```

-continued

```
<220> FEATURE:
<221> NAME/KEY: MISC_FEATURE
<222> LOCATION: (3)..(3)
<223> OTHER INFORMATION: Xaa can be His, Lys, or Tyr.

<400> SEQUENCE: 6

Xaa Xaa Xaa His Lys Met
1               5

<210> SEQ ID NO 7
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be Lys, Met, or Arg.
<220> FEATURE:
<221> NAME/KEY: MISC_FEATURE
<222> LOCATION: (2)..(2)
<223> OTHER INFORMATION: Xaa can be Lys.
<220> FEATURE:
<221> NAME/KEY: MISC_FEATURE
<222> LOCATION: (3)..(3)
<223> OTHER INFORMATION: Xaa can be His, Lys, or Tyr.

<400> SEQUENCE: 7

Xaa Xaa Xaa His Val Met
1               5

<210> SEQ ID NO 8
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be Lys, Met, or Arg.
<220> FEATURE:
<221> NAME/KEY: MISC_FEATURE
<222> LOCATION: (2)..(2)
<223> OTHER INFORMATION: Xaa can be Lys.
<220> FEATURE:
<221> NAME/KEY: MISC_FEATURE
<222> LOCATION: (3)..(3)
<223> OTHER INFORMATION: Xaa can be His, Lys, or Tyr.

<400> SEQUENCE: 8

Xaa Xaa Xaa Tyr Lys Met
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be Lys, Met, or Arg.
<220> FEATURE:
<221> NAME/KEY: MISC_FEATURE
<222> LOCATION: (2)..(2)
<223> OTHER INFORMATION: Xaa can be Lys.
<220> FEATURE:
<221> NAME/KEY: MISC_FEATURE
<222> LOCATION: (3)..(3)
<223> OTHER INFORMATION: Xaa can be His, Lys, or Tyr.
```

```
<400> SEQUENCE: 9

Xaa Xaa Xaa Tyr Pro Met
1               5

<210> SEQ ID NO 10
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be Lys, Met, or Arg.
<220> FEATURE:
<221> NAME/KEY: MISC_FEATURE
<222> LOCATION: (2)..(2)
<223> OTHER INFORMATION: Xaa can be Lys.
<220> FEATURE:
<221> NAME/KEY: MISC_FEATURE
<222> LOCATION: (3)..(3)
<223> OTHER INFORMATION: Xaa can be His, Lys, or Tyr.

<400> SEQUENCE: 10

Xaa Xaa Xaa Tyr Val Met
1               5

<210> SEQ ID NO 11
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa can be Lys, Met, or Arg.
<220> FEATURE:
<221> NAME/KEY: MISC_FEATURE
<222> LOCATION: (2)..(2)
<223> OTHER INFORMATION: Xaa can be Lys.
<220> FEATURE:
<221> NAME/KEY: MISC_FEATURE
<222> LOCATION: (3)..(3)
<223> OTHER INFORMATION: Xaa can be His, Lys, or Tyr.

<400> SEQUENCE: 11

Xaa Xaa Xaa Tyr Tyr Met
1               5

<210> SEQ ID NO 12
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P1
<220> FEATURE:
<221> NAME/KEY: PEPTIDE
<222> LOCATION: (1)..(6)
<223> OTHER INFORMATION: P1

<400> SEQUENCE: 12

Lys Lys His His Lys Met
1               5

<210> SEQ ID NO 13
```

```
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P2

<400> SEQUENCE: 13

Lys Lys His His Val Met
1               5

<210> SEQ ID NO 14
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P3

<400> SEQUENCE: 14

Lys Lys His Tyr Lys Met
1               5

<210> SEQ ID NO 15
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P4

<400> SEQUENCE: 15

Lys Lys His Tyr Pro Met
1               5

<210> SEQ ID NO 16
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P5

<400> SEQUENCE: 16

Lys Lys His Tyr Val Met
1               5

<210> SEQ ID NO 17
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P6

<400> SEQUENCE: 17
```

Lys Lys His Tyr Tyr Met
1               5

<210> SEQ ID NO 18
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P7

<400> SEQUENCE: 18

Lys Lys Tyr His Lys Met
1               5

<210> SEQ ID NO 19
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P8

<400> SEQUENCE: 19

Lys Lys Tyr His Val Met
1               5

<210> SEQ ID NO 20
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P9

<400> SEQUENCE: 20

Lys Lys Tyr Tyr Lys Met
1               5

<210> SEQ ID NO 21
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P10

<400> SEQUENCE: 21

Lys Lys Tyr Tyr Pro Met
1               5

<210> SEQ ID NO 22
<211> LENGTH: 6
<212> TYPE: PRT
<213> ORGANISM: Artificial sequence
<220> FEATURE:
<223> OTHER INFORMATION: Synthetic

```
<220> FEATURE:
<221> NAME/KEY: Peptide
<222> LOCATION: (1)..(6)
<223> OTHER INFORMATION: P11

<400> SEQUENCE: 22

Lys Lys Tyr Tyr Val Met
1               5

<210> SEQ ID NO 23
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P12

<400> SEQUENCE: 23

Lys Lys Tyr Tyr Tyr Met
1               5

<210> SEQ ID NO 24
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P13

<400> SEQUENCE: 24

Arg Lys Tyr His Lys Met
1               5

<210> SEQ ID NO 25
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P14

<400> SEQUENCE: 25

Arg Lys Tyr His Val Met
1               5

<210> SEQ ID NO 26
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P15

<400> SEQUENCE: 26

Arg Lys Tyr Tyr Lys Met
1               5
```

```
<210> SEQ ID NO 27
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P16

<400> SEQUENCE: 27

Arg Lys Tyr Tyr Pro Met
1               5

<210> SEQ ID NO 28
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P17

<400> SEQUENCE: 28

Arg Lys Tyr Tyr Val Met
1               5

<210> SEQ ID NO 29
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P18

<400> SEQUENCE: 29

Arg Lys Tyr Tyr Tyr Met
1               5

<210> SEQ ID NO 30
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P19

<400> SEQUENCE: 30

Met Lys Tyr His Lys Met
1               5

<210> SEQ ID NO 31
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P20
```

```
<400> SEQUENCE: 31

Met Lys Tyr His Val Met
1               5

<210> SEQ ID NO 32
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P21

<400> SEQUENCE: 32

Met Lys Tyr Tyr Lys Met
1               5

<210> SEQ ID NO 33
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P22

<400> SEQUENCE: 33

Met Lys Tyr Tyr Pro Met
1               5

<210> SEQ ID NO 34
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P23

<400> SEQUENCE: 34

Met Lys Tyr Tyr Val Met
1               5

<210> SEQ ID NO 35
<211> LENGTH: 6
<212> TYPE: PRT
<213> ORGANISM: Artificial sequence
<220> FEATURE:
<223> OTHER INFORMATION: Synthetic
<220> FEATURE:
<221> NAME/KEY: Peptide
<222> LOCATION: (1)..(6)
<223> OTHER INFORMATION: P24

<400> SEQUENCE: 35

Met Lys Tyr Tyr Tyr Met
1               5

<210> SEQ ID NO 36
<211> LENGTH: 6
<212> TYPE: PRT
<213> ORGANISM: Artificial sequence
<220> FEATURE:
```

```
-continued

<223> OTHER INFORMATION: Synthetic
<220> FEATURE:
<221> NAME/KEY: Peptide
<222> LOCATION: (1)..(6)
<223> OTHER INFORMATION: Control Peptide

<400> SEQUENCE: 36

Leu Phe Met Tyr His Pro
1               5
```